United States Patent
Kanayama et al.

(10) Patent No.: US 7,855,273 B2
(45) Date of Patent: Dec. 21, 2010

(54) METHOD FOR MANUFACTURING GELATIN WITH REDUCED ENDOTOXIN CONTENT AND LOW ENDOTOXIN GELATIN

(75) Inventors: Yoshitaka Kanayama, Sendai (JP); Yasuo Sakai, Sendai (JP)

(73) Assignee: Jellice Co., Ltd., Miyagi (JP)

( * ) Notice: Subject to any disclaimer, the term of this patent is extended or adjusted under 35 U.S.C. 154(b) by 203 days.

(21) Appl. No.: 11/681,323

(22) Filed: Mar. 2, 2007

(65) Prior Publication Data

US 2008/0132682 A1 Jun. 5, 2008

(30) Foreign Application Priority Data

Mar. 3, 2006 (JP) .............................. 2006-057656

(51) Int. Cl.
*C07K 14/78* (2006.01)
*C07K 1/14* (2006.01)

(52) U.S. Cl. ...................................... 530/355; 530/354
(58) Field of Classification Search ................. 530/354, 530/355

See application file for complete search history.

(56) References Cited

U.S. PATENT DOCUMENTS

| 4,082,737 A | 4/1978 | McGregor et al. |
| 4,307,013 A | 12/1981 | Ohtsuka et al. |
| 4,374,063 A | 2/1983 | Consolazio et al. |

FOREIGN PATENT DOCUMENTS

| JP | 56-68607 | 9/1981 |
| JP | 58-73371 | 5/1983 |
| JP | 2004-089448 | 3/2004 |
| JP | 2004-300077 | 10/2004 |
| JP | 2005-289841 | 10/2005 |
| JP | 2007-211170 | 8/2007 |

OTHER PUBLICATIONS

Petsch et al., "Endotoxin removal from protein solutions," J. of Biotechnology, 76, 2000, pp. 97-119.*
Pausa et al., "The endothelium is an extrahepatic site of synthesis of the seventh component of the complement system," Clin. Exp. Immunol. 121, 2000, pp. 69-76.*
Charles P. Gerba et al, Endotoxin Removal by Charge-Modified Filters, Applied and Environmetnal Microbiology, Dec. 1985, pp. 1375-1377, vol. 50, No. 6.
Kathleen J. Sweadner, et al, Fileration Removal of Endotoxin (Pyrogens) in Solution in Different States of Aggregation, Applied and Environmetnal Microbiology, Oct. 1977, pp. 382-385, vol. 34, No. 4.
Yoshitaka Kanayama et al, Development of Low Endotoxin Gelatin for Regenerative Medicine, Biol. Pharm. Bull. 30(2) 237-241 (Feb. 2007).
European Search Report, 07004405.2, mailed May 10, 2007.
Gorbet et al: "Endotoxin: The uninvited guest" Biomaterials, Elsevier Science Publisher BV., Barking, GB, vol. 26, No. 34, Dec. 2005, pp. 6811-6817, XP005000771 ISSN: 0142-9612.

* cited by examiner

*Primary Examiner*—Chih-Min Kam
(74) *Attorney, Agent, or Firm*—Ditthavong Mori & Steiner, P.C.

(57) ABSTRACT

A method of manufacturing gelatin with reduced endotoxin content. The method comprises processing a starting material gelatin-containing solution containing gelatin and an endotoxin with an ultrafiltration film having a molecular weight cut-off falling within a range of from 20,000 to 300,000 and having a molecular weight cut-off capable of passing at least a portion of the gelatin contained in the starting material gelatin-containing solution to obtain a permeate that is a gelatin-containing solution with a reduced endotoxin content. A gelatin having an average molecular weight falling within a range of 1,000 to 300,000 and an endotoxin content of less than 1 EU/mL per 1.0 percent of protein.

9 Claims, 2 Drawing Sheets

METHOD FOR MANUFACTURING GELATIN WITH REDUCED ENDOTOXIN CONTENT AND LOW ENDOTOXIN GELATIN

CROSS-REFERENCE TO RELATED APPLICATIONS

This application claims benefit of priority under 35 USC 119 to Japanese Patent Application No. 2006-57656 filed on Mar. 3, 2006, which is expressly incorporated herein by reference in its entirety.

BACKGROUND OF THE INVENTION

1. Field of the Invention

The present invention relates to a method for manufacturing gelatin with a reduced endotoxin content and to a low endotoxin gelatin.

2. Discussion of the Background

Gelatin, characterized by gelability, viscosity, foamability, adsorption-preventing capability, and the like, is a protein derived from natural substances that is employed in a variety of applications, such as foods, cosmetics, industrial products, and pharmaceuticals. In recent years, use as a cell and tissue scaffold (footing material) in regenerative treatments has also been anticipated. Cell and tissue scaffolds can be embedded as is at a site being regenerated, not only helping in the infiltration and proliferation of cells, but also playing a role in supporting cytokine as it guides cell differentiation and the like. However, use in such areas requires extremely high safety. The scaffold that is embedded is gradually degraded by proteases in the body and is controlled so as to be completely replaced by cells at the regeneration site over a period of several weeks. Since it remains within the body for an extended period in this manner, it has major effects not just on cells at the regeneration site, but on the entire body.

Normally, gelatins contain trace quantities of endotoxins. These are toxins that are present in extremely small quantities and exhibit intense heat-generating activity. Thus, when considering the use of gelatins in the realm of medical treatment, it is essential that the endotoxins be removed from the gelatin.

Endotoxins are comprised of lipopolysaccharide molecules. The molecular weight of the lipopolysaccharide subunits is said to be about 20,000. Endotoxins are deactivated by heat. However, to completely deactivate an endotoxin by heat requires heating to 250° C. for 30 minutes or more (Endotoxin Test Methods, Japanese Pharmacopoeia, 14th Ed., Revised). Known methods of deactivating endotoxins by methods other than heating include acid and base treatment methods (Japanese Unexamined Patent Publication (KOKAI) Showa No. 58-73371, which is expressly incorporated herein by reference in its entirety) in which endotoxins are degraded with an acid or a base, and methods employing acidic electrolytic water (Japanese Unexamined Patent Publication (KOKAI) No. 2004-089448, which is expressly incorporated herein by reference in its entirety). However, endotoxins are generally said to be stable relative to changes in pH.

Further, since the molecular weight of the lipopolysaccharide subunits of endotoxins is about 20,000, they cannot be removed by ordinary filtration (filtration precision: about 10 μm). Accordingly, the methods that are currently employed to remove them include distillation, reverse osmosis, and adsorption. However, the use of these methods to remove endotoxins from gelatin is difficult. Although distillation permits nearly complete removal of the endotoxins contained in water, it is not suited to removal of endotoxins from protein solutions. Reverse osmosis is incapable of passing even the amino acids constituting proteins, and is thus unsuited to filtering gelatins. Although there are adsorption methods such as applying a ZETA potential to a Nylon 66 film and filtering out the endotoxins by adsorption, in protein solutions such as gelatins, the intensity of the ions is greater than water and there are numerous factors affecting the removal rate of endotoxins, making it difficult to remove endotoxins with the same efficiency as from water (see Applied and Environmental Microbiology, Dec., p. 1375-1377 (1985), which is expressly incorporated herein by reference in its entirety).

The content of endotoxins is strictly regulated in injections administered directly into blood vessels. To remove endotoxins from such injections, neither reverse osmosis nor distillation is used; ultrafiltration is employed. In ultrafiltration, many of the lower molecules (antibiotics, salts, glucose, and the like) contained in injections can be completely passed while removing the endotoxins. In this process, the molecular weight cut-off of the ultrafiltration membrane employed is about several thousand, with a maximum of about 10,000 (Applied and Environmental Microbiology, Oct., p. 382-385 (1977), which is expressly incorporated herein by reference in its entirety; U.S. Pat. No. 4,082,737, which is expressly incorporated herein by reference in its entirety).

As set forth above, there are strict requirements for lowering the level of endotoxins in gelatin. Up to now, researchers cultivating cells and regenerative medical product manufacturers who purchase gelatins have been employing these various treatments. However, these treatments require great effort as well as being costly and time consuming. Thus, it is important to gelatin manufacturers to conduct suitable endotoxin-reducing treatments to ensure the quality of their products. However, thus far, there has been no known method for manufacturing gelatin with reduced endotoxin content that is suited to industrial production; the establishment of a method for readily manufacturing gelatin with reduced endotoxin content has become urgent.

Accordingly, an object of the present invention is to provide a method for manufacturing gelatin with reduced endotoxin content that is suited to large-quantity production. A further object of the present invention is to provide a gelatin with reduced endotoxin content.

The average molecular weight of gelatin obtained by gelling is at a minimum about 30,000 Daltons ("Da"). The use of an ultrafiltration membrane having a molecular weight cut-off of 10,000 Da to remove endotoxins contained in a solution of gelatin of such molecular weight is considered to be theoretically impossible. This is because, for example, even when processing gelatin with an average molecular weight of 30,000 Da with an ultrafiltration membrane with a molecular weight cut-off of 10,000 Da, it can be readily surmised that only the portion of ungelled gelatin with a molecular weight of 10,000 Da or less will be contained in the permeate, with the greater portion of the gelable gelatin remaining with the endotoxins in the retentate and ending up being eliminated.

In particular, the average molecular weight of commonly employed gelable gelatins is about 100,000. The removal of endotoxins by ultrafiltration membrane has been believed to be quite impossible. Further, since the molecular weight of the liposaccharide subunits of endotoxins is about 20,000, when the passing characteristics of an ultrafiltration membrane are taken into account, the reliable removal of endotoxins has been assumed to leave no margin in the selection of an ultrafiltration membrane with a molecular weight cut-off exceeding 10,000.

However, as a result of investigation conducted by the present inventors, it was discovered that in gelatin solutions, even when employing an ultrafiltration membrane with a molecular weight cut-off exceeding 10,000, the endotoxins remained in the retentate, making it possible to obtain a desired low endotoxin gelatin solution as permeate. That is, when gelatin solutions having various average molecular weights were prepared and then processed with several types of ultrafiltration membranes having molecular weight cut-offs ranging from 20,000 to 300,000 (molecular weight cut-offs permitting passage of at least a portion of the gelatin contained in the gelatin solution), the endotoxins remained in the retentate, and a gelatin solution of reduced endotoxin content was obtained as permeate.

In contrast to the low molecular weight substances (antibiotics, salts, glucose, and the like) targeted by the removal of endotoxins by conventional ultrafiltration, the present invention targets the removal of the endotoxins present in a gelatin solution. The amino acids constituting the gelatin exhibit various charge, hydrophobic, and hydrophilic properties. Thus, the state of endotoxins in the gelatin solution is thought to be one that tends to keep the endotoxins from passing through the ultrafiltration membrane. Thus, even with an ultrafiltration membrane having a molecular weight cut-off of 100,000 or 200,000, for example, which is far greater than the molecular weight of about 20,000 of the liposaccharide subunits of endotoxins, the endotoxins remain in the retentate and a desired low endotoxin gelatin solution is obtained as permeate. The present invention was devised on the basis of this completely unexpected result.

SUMMARY OF THE INVENTION

A feature of the present invention relates to a method of manufacturing gelatin with reduced endotoxin content, comprising processing a starting material gelatin-containing solution containing gelatin and an endotoxin with an ultrafiltration film having a molecular weight cut-off falling within a range of from 20,000 to 300,000 and having a molecular weight cut-off capable of passing at least a portion of the gelatin contained in said starting material gelatin-containing solution to obtain a permeate that is a gelatin-containing solution with a reduced endotoxin content.

Another feature of the present invention relates to a gelatin having an average molecular weight falling within a range of 1,000 to 300,000 and an endotoxin content of less than 1 EU/mL per 1.0 percent of protein.

Still another feature of the present invention relates to a coating; scaffold or matrix material; or microcapsule obtained employing as a starting material the above gelatin of the present invention; an additive for replacement plasma or a culture medium comprising the above gelatin of the present invention; a stabilizer or excipient comprising the above gelatin of the present invention; and a pharmaceutical comprising the stabilizer or excipient of the present invention.

The present invention permits the manufacturing of gelatin with reduced endotoxin by a method suited to large-quantity production. The present invention also provides a gelatin with reduced endotoxin.

By reducing endotoxins harmful to cell culturing without loss of the original gelability, bioaffinity, and biodegradability functions of gelatin, the present invention provides a material that adds a new quality (low endotoxins) to the conventional use domains of cell culturing and regenerative medical treatments.

Other exemplary embodiments and advantages of the present invention may be ascertained by reviewing the present disclosure and the accompanying drawings.

DESCRIPTIONS OF THE EMBODIMENTS

Figure 1:
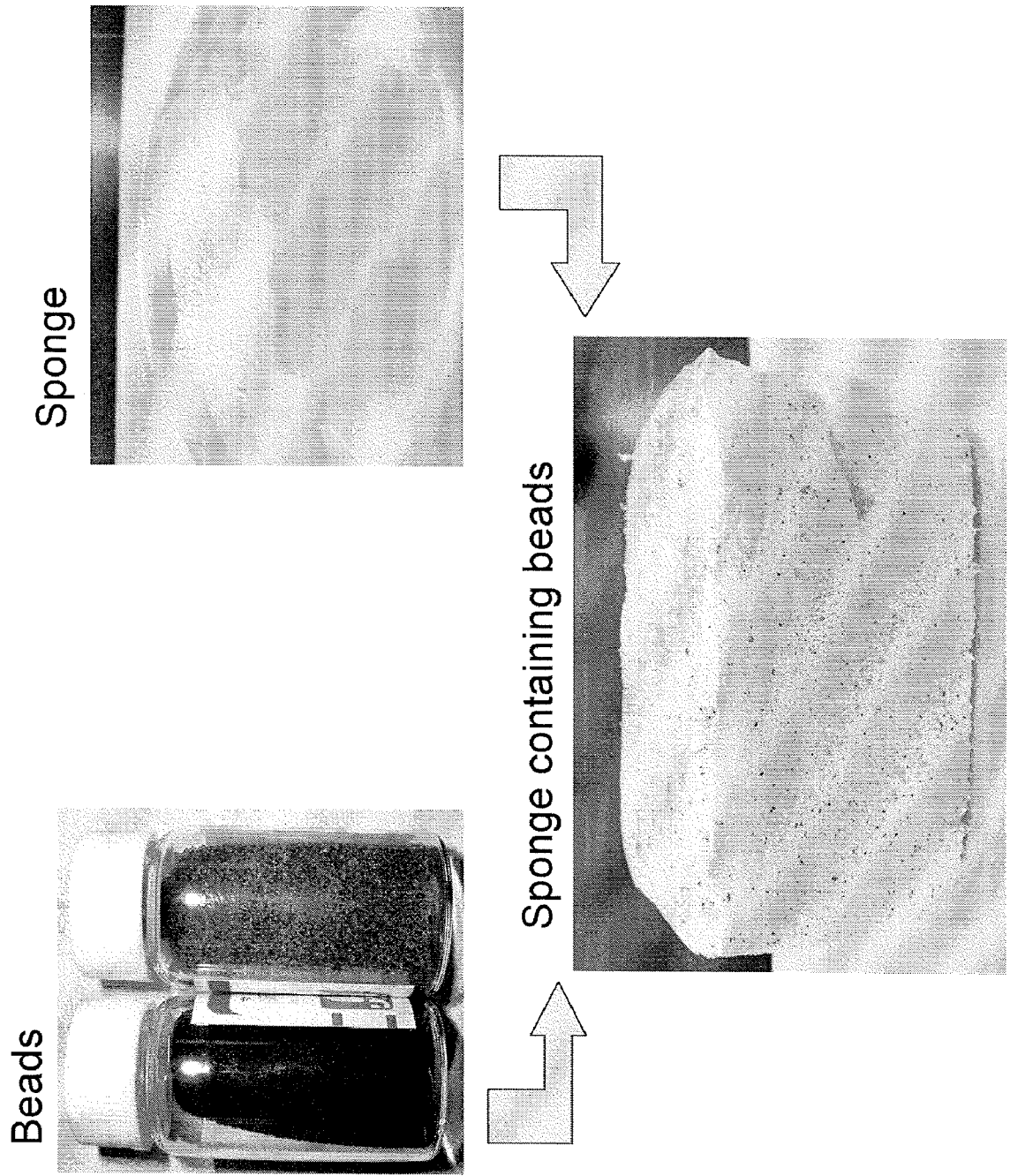
FIG. 1 is a sponge (upper right) and a sponge containing beads (bottom) prepared from low endotoxin gelatin as a starting material.

The following preferred specific embodiments are, therefore, to be construed as merely illustrative, and not limitative of the remainder of the disclosure in any way whatsoever. In this regard, no attempt is made to show structural details of the present invention in more detail than is necessary for the fundamental understanding of the present invention, the description taken with the drawings making apparent to those skilled in the art how the several forms of the present invention may be embodied in practice.

The method of the present invention is a method of manufacturing gelatin with reduced endotoxin content, comprising processing a starting material gelatin-containing solution containing gelatin and an endotoxin with an ultrafiltration film having a molecular weight cut-off falling within a range of from 20,000 to 300,000 and having a molecular weight cut-off capable of passing at least a portion of the gelatin contained in the starting-material gelatin containing solution to obtain a permeate that is a gelatin-containing solution with a reduced endotoxin content.

In chemical terms, an endotoxin is a lipopolysaccharide, the lipopolysaccharide subunits of which have a molecular weight of about 20,000 that is an important structural component of the outer membrane enclosing the peptidoglucan of the outer layer of Gram-negative bacteria. About $3 \times 10^5$ molecules (20 to 30 percent of the surface) are said to be present per cell. Endotoxins are considered to cause heat generation, mortality, shock, lowered blood pressure, and the like. As stated above, endotoxins are heat-resistant and exhibit powerful heat-generating activity in extremely small quantities.

The gelatin employed in the method of the present invention has an average molecular weight falling within a range of 1,000 to 300,000, for example. As will be described further below, a gelatin with an average molecular weight of about 30,000 or more is considered a gelable gelatin. Accordingly, gelable gelatins have an average molecular weight falling within a range of about 30,000 to 300,000. However, there are also various applications for gelatins without the ability to gel. The present invention can also be applied to gelatins without the ability to gel having an average molecular weight of 1,000 or greater but less than 30,000.

In the method of the present invention, the gelatin contained in the starting-material gelatin may have any average molecular weight falling within the above-stated range. As set forth above, there are cases where the molecular weight of the liposaccharide is much lower than the molecular weight of the gelatin employed in the method of the present invention (particularly for gelable gelatins having an average molecular weight of about 30,000 or more). Thus, conventional wisdom holds the two to be difficult to separate by filtration.

However, based on the results of investigation by the present inventors, as set forth above, the endotoxin in the gelatin solution permeates little or not at all through any ultrafiltration membrane having a molecular weight cut-off of anywhere from 20,000, equivalent to the roughly 20,000 molecular weight of the liposaccharide subunits, to about 300,000, or 15 times the molecular weight of roughly 20,000 of the lipopolysaccharide subunits, and thus appears to have a higher molecular weight in terms of filtration properties than does the gelatin. As a result, the endotoxin concentrates on the concentrated solution side, yielding a gelatin solution essentially not containing endotoxins as permeate (solution passing through the filter).

The solution containing the gelatin starting material comprising the endotoxin can be prepared by the following method, for example.

The gelatin starting material containing the endotoxin is not specifically limited other than that it be a gelatin containing an endotoxin. Commonly employed gelatins extracted with acids or alkalis from tissues such as the skin (dermis), tendon, bone, and cartilage of mammals, and gelatins extracted by identical methods from fish scales and fish skin, may be employed as the starting material. Gelatins obtained by known gelatin manufacturing methods, particularly those obtained without steps for removing or deactivating endotoxins, normally contain endotoxins.

Methods of preparing a gelatin solution used for removal of the endotoxins are described below. Gelatins in the form of pellets or the like are swollen with water at ordinary temperature, water (including brine) is added to a desired concentration, and the gelatin is dissolved in the water at a temperature of about 60° C., for example, to obtain a gelatin solution. When the gelatin is in the form of a powder, water (including water to which salt has been added) is added to a desired concentration without swelling, and the gelatin is dissolved in the water at a temperature of about 60° C. to obtain a gelatin solution. The liquid gelatin may be employed as is or adjusted to suitable concentration for use in the method of the present invention.

The solution containing the gelatin starting material is prepared by dissolving the gelatin starting material in plain water or brine. Additives may be added as needed. However, when preparing a pure gelatin, ultrafiltration is conducted without the addition of such additives.

The gelatin concentration in the solution containing the above-described gelatin starting material suitably falls, for example, within a range of 1 to 30 weight percent, desirably a range of 3 to 25 weight percent, and preferably, a range of 5 to 20 weight percent. When the gelatin concentration is excessively low, the concentration of the gelatin solution obtained also drops. For example, in the preparation of a solid gelatin, the viscosity of the solution containing the gelatin starting material increases, tending to render processing by ultrafiltration difficult. In particular, when the gelatin concentration exceeds 30 weight percent, the viscosity of the solution containing the gelatin starting material rises, sometimes compromising ultrafiltration properties. From this perspective, a gelatin concentration falling within the above-stated range is suitable.

Further, as stated above, endotoxin is thought to be present in the gelatin solution in a form that has a greater tendency not to pass through an ultrafiltration membrane than would be indicated by its original molecular weight. For example, the endotoxin is surmised to be in the form of a polymer aggregate. However, this has only been surmised, and the present inventors do not intend to limit themselves to such conjecture. The fact is, endotoxin tends not to pass through an ultrafiltration membrane having a molecular weight cut-off greatly exceeding the original molecular weight when in a gelatin solution.

The phenomenon whereby the endotoxin tends not to pass through an ultrafiltration membrane having a molecular weight cut-off greatly exceeding the original molecular weight in a gelatin solution has been confirmed for gelatin solutions having average molecular weights ranging from 1,000 to 300,000 at gelatin concentrations ranging from 1 to 30 weight percent. Accordingly, from this perspective, the gelatin concentration of the gelatin solution falling within a range of from 1 to 30 weight percent is suited.

The gelatin starting material will vary with the climate of the manufacturing country, the manufacturing environment, the animal of origin, the extraction method, the cleanliness of the equipment employed in extraction, and the like. However, many gelatin starting materials will contain 1,000 to 100,000 EU/mL of endotoxin per 1.0 percent of protein. The method of the present invention can remove nearly all of the endotoxin contained in gelatin. However, it is normally desirable to process gelatin containing 1,000 to 5,000 EU of endotoxin per 1.0 percent of protein, with gelatin containing 100 to 1,000 EU being preferred, gelatin containing 10 to 100 EU being of greater preference, and gelatin containing 1 to 10 EU being of even greater preference.

The molecular weight of the gelatin contained in the above-described starting material may, for example, range from 1,000 to 300,000. The average molecular weight of a gelatin that is obtained by extraction and purification from the bone or skin of an organism can be suitably determined by controlling the site of the starting materials, the extraction temperature and period, degradation of the gelatin by proteolases, and the like.

Gelatins with an average molecular weight of 1,000 or more but less than 10,000 are gelatins of relatively low molecular weight, such as gelatin peptides that have been degraded by proteolases or the like. Gelatins with such molecular weight distributions have extremely low viscosities and are not gelable. Despite not being gelable, they have a variety of applications.

Gelatins with an average molecular weight of 10,000 or more but less than 100,000 are gelatins of medium-low molecular weight; common gelatins fall into this category. Gelatins with an average molecular weight of 10,000 or more but less than 30,000 are gelatins of relatively low gelability and viscosity, with gelability and viscosity increasing with molecular weight. Gelatins with an average molecular weight of 30,000 or more have good gelability. Accordingly, from the perspective of having good gelability, the average molecular weight is desirably 30,000 or greater.

Gelatins with an average molecular weight of 100,000 or more but not exceeding 300,000 are gelatins of relatively high molecular weight. Examples are heat-denatured collagens (gelatins) in which molecular weight reduction by heat is suppressed, having a partially loosened triple-helix structure.

In the manufacturing method of the present method, a solution containing a gelatin starting material containing an endotoxin is processed with an ultrafiltration membrane having a molecular weight cut-off falling within a range of 20,000 to 300,000 that passes at least a portion of the gelatin contained in the solution containing starting material. Conventionally, the ultrafiltration membranes employed to remove endotoxins from injections and the like normally have molecular weight cut-offs of about several thousand, maximum 10,000. However, ultrafiltration membranes having a molecular weight cut-off falling within a range of 20,000 to 300,000 are employed in the present invention. An ultrafiltration membrane having a molecular weight cut-off falling within a range of 20,000 to 300,000 can remove the endotoxin in the gelatin solution with essentially none of the endotoxin passing into the permeate. However, the greater the molecular weight cut-off, depending on the conditions (gelatin concentration, average molecular weight of the gelatin, temperature, and the like), the greater the possibility that an extremely small quantity of endotoxin will pass through the ultrafiltration membrane. From the viewpoint of confirming removal of the endotoxin, the molecular weight cut-off of the ultrafiltration membrane is desirably less than or equal to 200,000.

However, the molecular weight cut-off of the ultrafiltration membrane is selected so that at least a portion of the gelatin contained in the starting material gelatin-containing solution passes through and desired gelatin is contained in the permeate. Desirably, an ultrafiltration membrane is employed that has a molecular weight cut-off that is 0.5-fold or more, preferably 0.8-fold or more, more preferably 1-fold or more the average molecular weight of the gelatin contained in the starting material gelatin-containing solution. The molecules that pass through the ultrafiltration membrane generally have a molecular weight falling within a range of plus or minus 50 percent of the molecular weight cut-off. For example, in the case of an ultrafiltration membrane having a molecular weight cut-off of 100,000, molecules having a molecular weight of 50,000 to 150,000 will be able to pass through.

When the molecular weight cut-off of the ultrafiltration membrane is greater than the average molecular weight of the gelatin in the gelatin solution, the filtration operation runs smoothly. As set forth above, the molecular weight of molecules that are fractionated by the ultrafiltration membrane falls within a range of plus or minus 50 percent of the molecular weight cut-off. The molecular weight cut-off of the ultrafiltration membrane is determined in consideration of these points, as well as the average molecular weight of the gelatin contained in the gelatin solution, and the average molecular weight of the desired gelatin in which the endotoxin content has been reduced. When the molecular weight cut-off of the ultrafiltration membrane is sufficiently higher than the average molecular weight of the gelatin in the gelatin solution, the average molecular weight of the gelatin in which the endotoxin quantity has been reduced will be roughly equivalent to the average molecular weight of the gelatin in the gelatin solution. By contrast, when the molecular weight cut-off of the ultrafiltration membrane is equal to or less than the average molecular weight of the gelatin in the gelatin solution, the average molecular weight of the gelatin with the reduced endotoxin content will sometimes be lower than the average molecular weight of the gelatin in the gelatin solution.

When the molecular weight cut-off of the ultrafiltration membrane employed is 30,000 or greater, the use of a gelatin solution in which the average molecular weight of the gelatin is 30,000 or greater permits the obtaining of a gelatin having a reduced endotoxin content and gelability. From the perspective of obtaining gelatin with reduced endotoxin content containing gelatin having gelability by a relatively smooth filtration operation, the molecular weight cut-off of the ultrafiltration membrane employed is desirably 50,000 or greater, preferably 80,000 or greater, and more preferably, 100,000 or greater. Further, the upper limit of the molecular weight cut-off of the ultrafiltration membrane is 300,000. However, as set forth above, the upper limit of the molecular weight cut-off is desirably 200,000, preferably 150,000.

When preparing a gelatin with reduced endotoxin content containing nongelable gelatin, an ultrafiltration membrane with a molecular weight cut-off of 20,000 to 300,000, desirably 25,000 to 200,000, and preferably 25,000 to 150,000 is suitably employed; a gelatin solution containing gelatin with an average molecular weight of 1,000 to 30,000 can be suitably ultrafiltered.

The ultrafiltration membrane employed in the present invention is not specifically limited other than that it has the above-stated molecular weight cut-off. For example, an ultrafiltration membrane comprised of regenerated cellulose, Nylon, hydrophilic polyethersulfone, and the like may be employed. Ultrafiltration membranes comprised of materials other than these may also be employed.

The filtration method in which an ultrafiltration membrane is employed is not specifically limited. For example, either dead-end filtration or cross-flow filtration may be employed. However, from the perspective of the processing level, the cross-flow method is preferred. The cross-flow method may be employed in the form of a cassette, spiral cartridge, or fiber flow.

With a cassette-type ultrafiltration membrane, the filtration membrane is built into a flat cassette and filtration is conducted with the solution flowing parallel to the surface of the membrane while contaminants are removed. Examples of principal products are the Pericon 2 cassette made by Millipore and the flat sheet Kvick cassette made by Amersham Biosciences (Ltd.). In this type of ultrafiltration, a pressure gauge and a solution delivery tube are connected to a dedicated holder sandwiching the cassette, and a suitable solution delivery pump is employed to conduct the ultrafiltration operation. In the actual operation, the output of the solution delivery pump is adjusted so as not to exceed the maximum pressure of the ultrafiltration membrane within the cassette employed to implement the ultrafiltration operation. This can be conducted according to the basic method described in the operating manual or the like. The low endotoxin gelatin obtained by the present invention can also be obtained by processing gelable gelatins. Thus, it is important to maintain the starting-material gelatin solution and permeate at a certain temperature during the operation so that they do not gel. Suitable insulating and thermostatic devices are thus desirable in addition to basic equipment. Raising the maintenance temperature lowers viscosity and facilitates filtration, but the temperature is adjusted so as not to exceed the heat resistance limit of the ultrafiltration membrane within the cassette. The processing level may be selected as desired based on the area of the membrane in the cassette employed and the number of cassettes employed.

In the method employing a cassette-type ultrafiltration membrane, for example, permeate is poured in quantities of 1.0 L into bottles that have been sterilized with dry heat for 2 hours at 250° C. and the concentration of the gelatin in each bottle is measured. The fraction in which gelatin that has been filtered is contained is reliably determined from the gelatin concentration. It is possible to collect only those filtered fractions containing gelatin to obtain the targeted low endotoxin gelatin solution. Since extremely small quantities of endotoxin are contained in the filtered fraction solutions, it is appropriate to measure the endotoxin concentration for quality control. The permissible residual endotoxin concentration varies with the application of the gelatin obtained. However, for example, it may be less than 1 EU/mL, desirably less than 0.1 EU/mL, preferably less than 0.05 EU/mL, and more preferably, less than 0.03 EU/mL.

In ultrafiltration membranes of the spiral cartridge type, the filtration membrane is built into a cylindrical cassette in spiral fashion and filtration is conducted with the solution flowing parallel to the surface of the membrane while contaminants are removed. An example of a major product is Helicon made by Millipore. In this type, no holder is required; a pressure gauge and a solution delivery tube are connected to the cylindrical cassette and a suitable solution delivery pump is employed to conduct the ultrafiltration operation. The actual ultrafiltration operation is conducted by adjusting the output of the solution delivery pump so as not to exceed the maximum pressure of the ultrafiltration membrane in the cassette employed. This can be conducted according to the basic method described in the operating manual or the like. The low endotoxin gelatin obtained by the present invention can also be obtained by processing gelable gelatins. Thus, it is important to maintain the starting-material gelatin solution and permeate at a certain temperature during the operation so that they do not gel. Suitable insulating and thermostatic devices are thus desirable in addition to basic equipment. Raising the maintenance temperature lowers viscosity and facilitates filtration, but the temperature is adjusted so as not to exceed the heat resistance limit of the ultrafiltration membrane within the cassette. The processing level may be selected as desired based on the area of the membrane employed.

In methods employing ultrafiltration membranes of the spiral cartridge type, for example, permeate is poured in quantities of 1.0 L into bottles that have been sterilized with dry heat for 2 hours at 250° C. and the concentration of the gelatin in each bottle is measured. The fraction in which gelatin that has been filtered is contained is reliably determined from the gelatin concentration. It is possible to collect only those filtered fractions containing gelatin to obtain the targeted low endotoxin gelatin solution. Since extremely small quantities of endotoxin are contained in the filtered fraction solutions, it is appropriate to measure the endotoxin concentration for quality control. The permissible residual endotoxin concentration varies with the application of the gelatin obtained. However, for example, it may be less than 1 EU/mL, desirably less than 0.1 EU/mL, preferably less than 0.05 EU/mL, and more preferably, less than 0.03 EU/mL.

In ultrafiltration membranes of the fiber flow type, the filtration membrane is built into a cylindrical cassette as a bundle of long, hollow tubes and filtration is conducted with the solution flowing parallel to the surface of the membrane while contaminants are removed. An example of a major product is the hollow fiber cartridge made by Amersham Biosciences (Ltd.) and Microza made by Asahi Kasei (Ltd.). In this type of ultrafiltration, no holder is required; a pressure gauge and a solution delivery tube are connected to the cylindrical cassette and a suitable solution delivery pump is employed to conduct the ultrafiltration operation. The actual ultrafiltration operation is conducted by adjusting the output of the solution delivery pump so as not to exceed the maximum pressure of the ultrafiltration membrane in the cassette employed. This can be conducted according to the basic method described in the operating manual or the like. The low endotoxin gelatin obtained by the present invention can also be obtained by processing gelable gelatins. Thus, it is important to maintain the starting-material gelatin solution and permeate at a certain temperature during the operation so that they do not gel. Suitable insulating and thermostatic devices are thus desirable in addition to basic equipment. Raising the maintenance temperature lowers viscosity and facilitates filtration, but the temperature is adjusted so as not to exceed the heat resistance limit of the ultrafiltration membrane within the cassette. The processing level may be selected as desired based on the area of the membrane employed.

In methods employing ultrafiltration membranes of the fiber flow type, for example, permeate is poured in quantities of 1.0 L into bottles that have been sterilized with dry heat for 2 hours at 250° C. and the concentration of the gelatin in each bottle is measured. The fraction in which gelatin that has been filtered is contained is reliably determined from the gelatin concentration. It is possible to collect only those filtered fractions containing gelatin to obtain the targeted low endotoxin gelatin solution. Since extremely small quantities of endotoxin are contained in the filtered fraction solutions, it is appropriate to measure the endotoxin concentration for quality control. The permissible residual endotoxin concentration varies with the application of the gelatin obtained. However, for example, it may be less than 1 EU/mL, desirably less than 0.1 EU/mL, preferably less than 0.05 EU/mL, and more preferably, less than 0.03 EU/mL.

Although determined in consideration of the viscosity of the gelatin solution and the heat resistance temperature of the membrane, processing with the ultrafiltration membrane is normally conducted at a temperature of 20 to 60° C., preferably 40 to 50° C. Conducting processing with the ultrafiltration membrane within this temperature range not only affords the advantage of keeping liquid those polymer gelatins that gel, but also shortens the filtration processing time by lowering the viscosity.

The method of the present invention yields a gelatin-containing solution with an endotoxin content reduced to less than 1 EU, desirably less than 0.1 EU, more preferably less than 0.05 EU, and most preferably, less than 0.03 EU, per 1.0 percent of protein in the form of the permeate of an ultrafiltration membrane. The gelatin contained in the gelatin-containing solution changes based on the average molecular weight of the starting material gelatin, the molecular weight cut-off of the ultrafiltration membrane, and the like; however, an average molecular weight ranging from 1,000 to 300,000 can be obtained.

The solution that does not pass through the ultrafiltration membrane (the concentrated solution) contains a higher concentration of endotoxins than the starting material. Accordingly, it can be discarded, or employed as a starting material for gelatin in a field of use in which endotoxins have no effect.

The present invention covers gelatins containing less than 1 EU of endotoxin per 1.0 percent of protein. The gelatin of the present invention desirably contains less than 0.1 EU, preferably less than 0.05 EU, and more preferably, less than 0.03 EU, of endotoxin per 1.0 percent of protein. The gelatin may have an average molecular weight ranging from 1,000 to 300,000. Based on average molecular weight, the gelatin can be divided into: (1) relatively low molecular weight gelatins having an average molecular weight of 1,000 or more but less than 10,000; (2) medium molecular weight gelatins having an average molecular weight of 10,000 or more but less than 100,000; and (3) relatively high molecular weight gelatins having an average molecular weight of 100,000 or more but not more than 300,000.

Since the quantity of endotoxin is reduced in the gelatin of the present invention and in gelatin produced by the method of the present invention, these gelatins can be suitably employed in medical devices, as starting materials for cell and tissue processing pharmaceuticals, and as bases for use in formulating pharmaceuticals and the like. Additionally, they may be suitably employed in cosmetics, topical pharmaceuticals, and foods. The method of the present invention may be used to process collagen protein instead of gelatin to prepare collagen protein with reduced endotoxin.

The present invention covers spongelike, sheetlike, filmlike, blocklike, and fibrous materials obtained employing the gelatin of the present invention as a starting material, for example. Spongelike, sheetlike, filmlike, blocklike, and fibrous materials can be prepared as follows.

Such materials are suited to regenerative medical treatment uses. The term "regenerative medical treatment uses" means, for example, use to promote the healing of wounds in recessed areas by embedding a product that has been processed into spongelike form for deep tissue losses and grafts for dermal loss; use to promote a moist environment by adhering a product that has been processed into sheetlike form on the afflicted area of a burn wound, such as a wound dressing; and use to promote the healing of wounds. The spongelike, sheetlike, filmlike, blocklike, or fibrous material obtained employing the gelatin of the present invention as a starting material may be employed in artificial organs and artificial tissue for regenerative medical treatment. Examples of artificial organs and tissues are: artificial skin, bone, cartilage, tendons, blood vessels, livers, ligaments, mammary glands, heart valves, tracheae, corneas, and peridontal tissue.

The present invention relates to coatings; scaffold and matrix materials; and microcapsules obtained employing the gelatin of the present invention as a starting material, for example. Coatings as well as scaffold and matrix materials processed into sponge or sheet form are suited for use in cell culturing. Microcapsules are employed in DDS formulations.

The present invention relates to substitute plasma and culture medium-use additives containing the gelatin of the present invention, for example. The term "substitute plasma" refers to products employed to assist in blood transfusions to prevent a reduction in the amount of circulating blood during a loss of blood, such as serum albumin and dextran. Examples of additives for use in culture media are functional substances, stabilizers, and the like that are added to enhance the proliferation capability and metabolic functions of the cells being cultured. Bovine plasma albumin and the like are employed as stabilizers. However, the utilization of products in which the endotoxin has been reduced to reduce cell toxicity yields a better culture environment for the cells.

The present invention also relates to a stabilizer and an excipient containing the gelatin of the present invention. The stabilizer and excipient are employed in pharmaceuticals.

EXAMPLES

The present invention is specifically described below. However, the present invention is not limited to the Examples.

Example 1

Acid-treated pig skin gelatins manufactured by Jellice Corp. (average molecular weights: 100,000, 80,000, 60,000, and 40,000) were prepared to 12 percent (W/V), 10 mL quantities were poured onto CENTRI PLUS (molecular weight cut-offs: 100,000 and 50,000) membranes made by Millipore, and centrifugation was conducted at 50° C. and 3,000 rpm for 20 minutes. The endotoxin in the permeate was measured with a kit for measurement of endotoxin content made by Cambrex Bio Science Waldersville, Inc. according to the operating manual of the kit by calorimetric determination (kit employed: Kinetic-QCL; plate reader: Kinetic-QCL Reader; software: Kinetic-QCL software) using microplates and by gel inversion (kit employed: PYROGENT 03 Plus). Gelability was determined by storing the permeate overnight at 4° C. and touching it the next day. The results are given in Table 1.

Colorimetric Determination Method

1. Pyrogen-free water (Japanese Pharmacopoeia, injection-use water, Otsuka distilled water, made by Otsuka Pharmaceutical Factory, Inc.) that had been returned to room temperature was added to achieve an *E. coli* toxin vial potency in Kinetic-QCL of 50 EU/mL and the mixture was stirred vigorously for 5 minutes in a test tube mixer and the like. This was employed as stock solution.
2. After vigorously stirring the stock solution (after being returned to room temperature when refrigerated) for one minute, diluted solutions with potencies of 5, 0.5, 0.05, and 0.005 EU/mL were immediately prepared. These, along with the stock solution, were employed as standard endotoxin solutions. Only pyrogen-free water was employed in preparation. Following dilution, stirring was conducted for one minute or more until fractionation.
3. Diluted solutions of each of the samples were prepared using pyrogen-free water.
4. A personal computer connected to a plate reader (the plate reader could also be operated directly) was used to run Kinetic-QCL software and various test parameters were entered.
5. Based on display instructions, necessary items relating to the reagents and test samples were inputted.
6. Pyrogen-free water (blank), standard endotoxin samples, test samples, and positive controls were poured in quantities of 100 μL each into the wells of a microplate.
7. The microplates containing the various solutions were placed in the Kinetic-QCL Reader and the plates were then placed in a culture chamber.
8. The plates were preprocessed (heated) for 10 minutes.
9. During processing, 2.6 mL of pyrogen-free water was gently added to the LAL/color-developing synthetic substrate vial within the Kinetic-QCL and mixing and dissolution were conducted while exercising care to prevent foaming.
10. When the preprocessing had been completed, the plate was removed and 100 μL of LAL/color-developing synthetic matrix was added to each well.
11. A Kinetic-QCL test was conducted according to the software.
12. The Kinetic-QCL Reader continuously measured the absorbance at 405 nm of each of the wells in the microplate. The initial absorbance of each well was taken as a blank, and the time required for the absorbance to increase to 0.200 was adopted as the reaction time.
13. The log/log function of the reaction time and endotoxin concentration obtained for each of the standard endotoxin solutions was calculated. A calibration curve plotted on that basis was employed to calculate the levels of endotoxin in each of the samples.

Gel Inversion Method

1. A 5.2 mL quantity of pyrogen-free water (Japanese Pharmacopoeia, injection-use water, Otsuka distilled water, made by Otsuka Pharmaceutical Factory, Inc.) was gently added to the LAL reagent in PYROGENT 03 Plus and thorough mixing and dissolution were conducted while exercising care to prevent foaming. Once adequate dissolution had been achieved, 100 μL of solution was poured into endotoxin-free test tubes (sterilized with dry heat for 2 hours at 250° C., 12×75 mm).

Immediately after pouring, endotoxin-free caps (sterilized with dry heat for 2 hours at 250° C.) were applied. The test tubes were then placed in frozen storage at −80° C., and removed when needed for use.

2. Pyrogen-free water was added to achieve an *E. coli* toxin vial potency in PYROGENT 03 Plus of 20 EU/mL and the mixture was stirred vigorously for 15 minutes in a test tube mixer and the like. This was employed as stock solution.
3. The endotoxin stock solution was diluted to prepare standard endotoxin solutions (ex. 0.2 EU/mL).

4. Diluted solutions of various samples were prepared with pyrogen-free water.
5. To test tubes containing LAL reagent were charged 100 μL each of pyrogen-free water (blank), standard endotoxin solution, and test samples
6. Incubation was conducted for 1 hour at 37° C.±1° C.
7. With the conclusion of incubation, the test tubes were rapidly inverted 180° and the degree of gelling was observed.

TABLE 1

| Average molecular weight of starting material gelatin | | 100,000 | 80,000 | 60,000 | 40,000 |
|---|---|---|---|---|---|
| Endotoxin content (EU/mL) per 1.0 percent | | 2,000 | 1,842 | 1542 | 1,808 |
| Molecular weight cut-off of ultrafiltration membrane: 100,000 | Endotoxin content of permeate (EU/mL) | Less than 0.03 | Less than 0.03 | Less than 0.03 | Less than 0.03 |
| Molecular weight cut-off of ultrafiltration membrane: 50,000 | Endotoxin content of permeate (EU/mL) | Did not pass through membrane; measurement precluded | Did not pass through membrane; measurement precluded | Less than 0.03 | Less than 0.03 |

As will be understood from the results given in the above table, when an ultrafiltration membrane with a molecular weight cut-off of 100,000 was employed, the endotoxin concentration in the permeate was less than 0.03 EU/mL in all cases and gelling occurred in all cases. Further, the endotoxin content increased relative to the initial level in gelatin solutions that were incapable of passing through the filtration membrane (non-permeating solutions).

When an ultrafiltration membrane with a molecular weight cut-off of 50,000 was employed, gelatins with average molecular weights of 100,000 and 80,000 were almost completely unable to pass through the filtration membranes. Gelatins with average molecular weights of 60,000 and 40,000 produced permeates with endotoxin concentrations of less than 0.03 EU/mL.

The molecular weight cut-off of the ultrafiltration membrane and the average molecular weight of gelatins that can be filtered through can be determined with reference to the above results.

Example 2

Acid-treated pig skin gelatin manufactured by Jellice Corp. (average molecular weight: 60,000) was prepared to 12 percent (W/V) and 20 L was subjected to ultrafiltration with a Proflux M30 made by Millipore. The ultrafiltration membrane employed was a spiral cartridge made by Millipore (molecular weight cut-off 100,000). The output of the solution delivery pump was adjusted so as not to exceed the maximum pressure. The ultrafiltration operation was conducted while maintaining the temperature of the solution being delivered at 50° C.

Since the present invention permits the processing of gelable gelatins to obtain low endotoxin gelatins, it is important to maintain a temperature during the ultrafiltration operation that will not cause the gelatin solution of the material or the permeate to gel.

Raising the maintenance temperature lowers viscosity and facilitates filtration, but the temperature was adjusted so as not to exceed the heat resistance limit of the ultrafiltration membrane. For example, in the case of a membrane made of regenerated cellulose, the heat resistance temperature was 55.0° C. and ultrafiltration was conducted with an upper limit of 50° C.

In filtration, 1.0 L was poured into individual bottles that had been sterilized with dry heat for 2 hours at 250° C., and the gelatin concentration and endotoxin concentration of each bottle were measured. As a result, the permeate obtained in the first several bottles exhibited an extremely low gelatin concentration, so these bottles were discarded. The 15 bottles (15 L) of permeate with stable gelatin concentrations and endotoxin concentrations of less than 0.03 EU/mL were admixed to obtain the targeted low endotoxin gelatin. As a result, by conducting ultrafiltration of starting-material gelatin with an endotoxin content of 1,542 EU/mL, it was possible to obtain a gelatin permeate reduced to less than 0.03 EU/mL. As in Example 1, the concentrated gelatin solution that did not pass through the filter had a higher endotoxin content than it initially had.

Example 3

Acid-treated pig skin gelatin manufactured by Jellice Corp. (average molecular weight: 60,000) was prepared to 12 percent (W/V) and 20 L was subjected to ultrafiltration with a Pericon miniholder system made by Millipore. The ultrafiltration membrane employed was a Pericon 2 minifilter made by Millipore (molecular weight cut-off 100,000). During the ultrafiltration operation, the output of the solution delivery pump was adjusted so as not to exceed the maximum pressure.

Since the present invention permits the processing of gelable gelatins to obtain low endotoxin gelatins, it is important to maintain a temperature during the ultrafiltration operation that will not cause the gelatin solution of the material or the permeate to gel.

Raising the maintenance temperature lowers viscosity and facilitates filtration, but the temperature was adjusted so as not to exceed the heat resistance limit of the ultrafiltration membrane. A 1.0 L quantity was poured into individual bottles that had been sterilized for 2 hours with dry heat at 250° C. and the gelatin concentration and endotoxin concentration of each of the bottles were measured. As a result, the permeate obtained in the first several bottles exhibited an extremely low gelatin concentration, so these bottles were discarded. The 15 bottles (15 L) of permeate with stable gelatin concentrations and endotoxin concentrations of less than 0.03 EU/mL were admixed to obtain the targeted low endotoxin gelatin. As a result, by conducting ultrafiltration of starting-material gelatin with an endotoxin content of 1,542 EU/mL, it was possible to obtain a gelatin permeate reduced to less than 0.03 EU/mL. As in Example 1, the concentrated gelatin solution that did not pass through the filter had a higher endotoxin content than it initially had.

Example 4

Acid-treated pig skin gelatins manufactured by Jellice Corp. (average molecular weights: 1,000 to 2,000) were prepared to 12 percent (W/V) and 20 L was subjected to ultrafiltration with a Proflux M30 made by Millipore. The ultrafiltration membrane employed was a spiral cartridge made by Millipore (molecular weight cut-off 10,000). During the ultrafiltration operation, the output of the solution delivery pump was adjusted so as not to exceed the maximum pressure.

Raising the maintenance temperature lowers viscosity and facilitates filtration, but the temperature was adjusted so as not to exceed the heat resistance limit of the ultrafiltration membrane. A 1.0 L quantity was poured into individual bottles that had been sterilized for 2 hours with dry heat at 250° C. and the gelatin concentration and endotoxin concentration of each of the bottles were measured. As a result, the permeate obtained in the first several bottles exhibited an extremely low gelatin concentration, so these bottles were discarded. The 15 bottles (15 L) of permeate with stable gelatin concentrations and endotoxin concentrations of less than 0.03 EU/mL were admixed to obtain the targeted low endotoxin gelatin. As a result, by conducting ultrafiltration of starting-material gelatin with an endotoxin content of 1,850 EU/mL, it was possible to obtain a gelatin permeate reduced to less than 0.03 EU/mL. As in Example 1, the concentrated gelatin solution that did not pass through the filter had a higher endotoxin content than it initially had.

Example 5

Gelatins manufactured by Jellice Corp. (average molecular weights: 50,000 and 80,000) were prepared to 10 percent (W/V) and 20 L was subjected to ultrafiltration with a Pericon miniholder system made by Millipore. The ultrafiltration membrane employed was a Pericon 2 minifilter made by Millipore (molecular weight cut-off 300,000). During the ultrafiltration operation, the output of the solution delivery pump was adjusted so as not to exceed the maximum pressure.

Raising the maintenance temperature lowers viscosity and facilitates filtration, but the temperature was adjusted so as not to exceed the heat resistance limit of the ultrafiltration membrane. A 1.0 L quantity was poured into individual bottles that had been sterilized for 2 hours with dry heat at 250° C. and the gelatin concentration and endotoxin concentration of each of the bottles were measured. As a result, the permeates obtained in the first several bottles for both the 50,000 and 80,000 gelatins exhibited an extremely low gelatin concentration, so these bottles were discarded. The 15 bottles (15 L) of permeate with stable gelatin concentrations and endotoxin concentrations of less than 0.03 EU/mL were admixed to obtain the targeted low endotoxin gelatin. As a result, by conducting ultrafiltration of starting-material gelatin with an endotoxin content of 2,950 EU/mL, it was possible to obtain a gelatin permeate reduced to less than 0.03 EU/mL. As in Example 1, the concentrated gelatin solution that did not pass through the filter had a higher endotoxin content than it initially had.

Example 6

Gelatins manufactured by Jellice Corp. (average molecular weights: 50,000 and 80,000) were prepared to 5 percent (W/V) and 20 L was subjected to ultrafiltration with a Pericon miniholder system made by Millipore. The ultrafiltration membranes employed were Pericon 2 minifilters made by Millipore (molecular weight cut-offs 30,000 and 100,000). During the ultrafiltration operation (40° C.), the output of the solution delivery pump was adjusted so as not to exceed the maximum pressure. A 1.0 L quantity was poured into individual bottles that had been sterilized for 2 hours with dry heat at 250° C. and the gelatin concentration and endotoxin concentration of each of the bottles were measured.

As a result, the permeates obtained for both the 50,000 and 80,000 gelatins when using either the ultrafiltration membrane with a molecular weight cut-off of 30,000 or that with a molecular weight cut-off of 100,000 yielded gelatin permeates in which the endotoxin had been reduced to less than 0.03 EU/mL. The concentrated gelatin solution that did not pass through the filter had greater endotoxin activity than it initially had.

Example 7

A gelatin sponge was produced using the low endotoxin gelatin obtained in Example 2.

Gelatin Sponge Preparation Method
(1) Solutions with 0.1 to 20 percent gelatin concentrations were prepared.
(2) While cooling with ice water or the like (or at ordinary temperature), rapid stirring was conducted with a hand mixer or homogenizer (AM-7, made by Nissei Corporation) for 1 to 5 minutes.
(3) The solutions were poured into molds and frozen at −50 to −80° C.
(4) The completely frozen solutions were dried with a freeze dryer (FDU-830, made by EYELA).
(5) The dried product was crosslinked by thermal crosslinking, using a crosslinking agent, or the like, to obtain a gelatin sponge (upper right, FIG. 1).

Example 8

Figure 2:
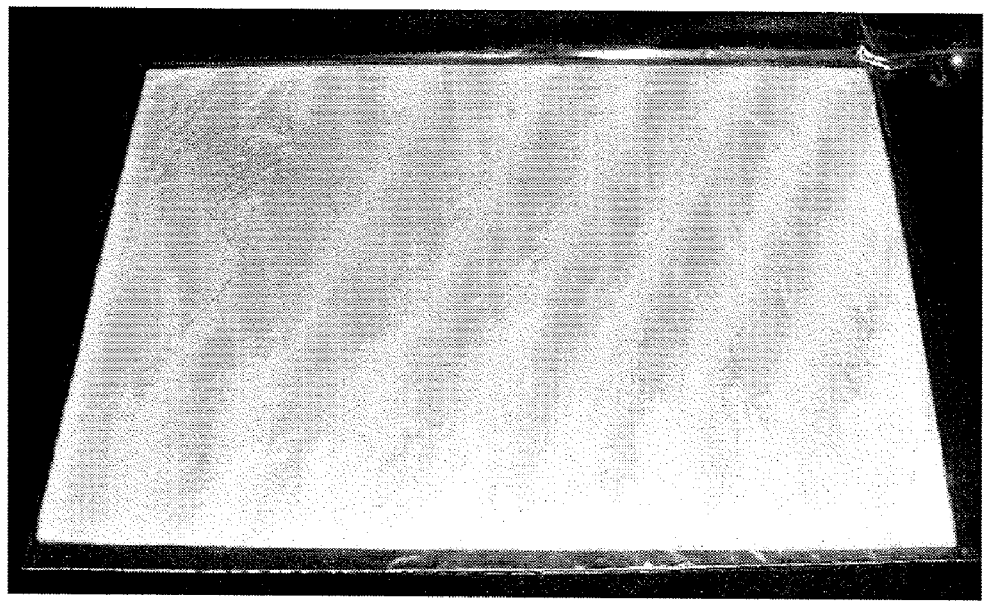
FIG. 2 is a sheet prepared from low endotoxin gelatin as a starting material.

A gelatin sheet was prepared using the low endotoxin gelatin obtained in Example 2.
The method of preparation was identical to that in Example 7. However, a shallow mold was employed (FIG. 2).

Example 9

A gelatin sponge was prepared by admixing beads containing an active ingredient with the low endotoxin gelatin obtained in Example 2.

Method of Preparing Sponge Containing Beads
(1) Solutions with 0.1 to 20 percent gelatin concentrations were prepared.
(2) While cooling with ice water or the like (or at ordinary temperature), rapid stirring was conducted with a hand mixer or homogenizer (AM-7, made by Nissei Corporation) for 1 to 5 minutes.
(3) The beads were added.

(4) The solutions were poured into molds and frozen at −50 to −80° C.
(5) The completely frozen solutions were dried with a freeze dryer (FDU-830, made by EYELA).
(6) The dried product was crosslinked by thermal crosslinking, using a crosslinking agent, or the like, to obtain a gelatin sponge containing beads (bottom, FIG. 1).

Example 10

Figure 3:
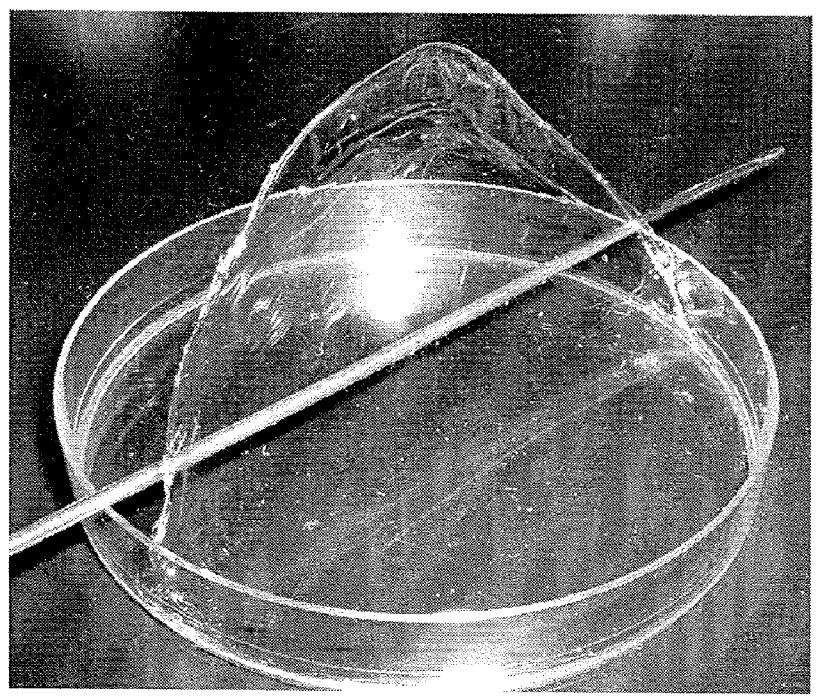
FIG. 3 is a culture Petri dish coated with low endotoxin gelatin.

The low endotoxin gelatin obtained in Example 2 was diluted with pyrogen-free water (Japanese Pharmacopoeia, injection-use water, Otsuka distilled water, made by Otsuka Pharmaceutical Factory, Inc.) to prepare 5.0 percent solutions. The lids were placed on thick culture Petri dishes (As One Corporation) 85 mm in diameter in a clean bench, and 3.0 mL of the gelatin solutions that had been prepared were added and extended. The remaining portions of the gelatin solutions were removed by pipet, and with the lids still on, drying was conducted at room temperature. This yielded culture Petri dishes coated with low endotoxin gelatins (FIG. 3).

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of manufacturing gelatin with reduced endotoxin content, wherein the molecular weight of the liposaccharide subunits of the endotoxin is about 20,000 Da,
    comprising processing a starting material gelatin-containing solution containing gelatin,
    wherein the average molecular weight of said geletan contained in said starting material gelatin-containing solution is in a range of from 30,000 to 300,000 Da, and
    an endotoxin with an ultrafiltration membrane having a molecular weight cut-off falling within a range of from 50,000 to 300,000 Da and having a molecular weight cut-off capable of passing at least a portion of the gelatin contained in the starting material gelatin-containing solution to obtain a permeate that is a gelatin-containing solution with a reduced endotoxin content, wherein the gelatin concentration in said starting material gelatin-containing solution is in a range of 1 to 30 weight percent.

2. The method according to claim 1, wherein the average molecular weight of said gelatin contained in said starting material gelatin-containing solution is in a range of from 30,000 to 200,000 Da.

3. The method according to claim 1, wherein the molecular weight cut-off of said ultrafiltration membrane is in a range of 50,000 to 150,000 Da.

4. The method according to claim 1, wherein the gelatin concentration in said starting material gelatin-containing solution is in a range of 5 to 20 weight percent.

5. The method according to claim 1, wherein said ultrafiltration membrane has a molecular weight cut-off of between 0.5 times or more and 10 times or less the average molecular weight of the gelatin contained in said starting material gelatin-containing solution.

6. The method according to claim 1, wherein said starting material gelatin-containing solution contains 1,000 to 100,000 EU/mL of endotoxin per 1.0 percent of protein.

7. The method according to claim 1, wherein said gelatin with reduced endotoxin content contains less than 1 EU/mL of endotoxin per 1.0 percent of protein.

8. The method according to claim 1, wherein said processing with an ultrafiltration membrane is conducted in the form of a cassette, spiral cartridge, or fiber flow.

9. The method according to claim 1, wherein said processing with an ultrafiltration membrane is conducted at 20 to 60° C.

* * * * *